(12) United States Patent
LePivert (10) Patent No.: US 8,380,299 B2
(45) Date of Patent: Feb. 19, 2013

(54) FLUID FLOWING DEVICE AND METHOD FOR TISSUE DIAGNOSIS OR THERAPY

(75) Inventor: Patrick LePivert, Jupiter, FL (US)

(73) Assignee: Nuvue Therapeutics, Inc., Fairfax, VA (US)

( * ) Notice: Subject to any disclaimer, the term of this patent is extended or adjusted under 35 U.S.C. 154(b) by 243 days.

(21) Appl. No.: 12/182,472

(22) Filed: Jul. 30, 2008

(65) Prior Publication Data
US 2009/0036823 A1    Feb. 5, 2009

Related U.S. Application Data

(60) Provisional application No. 60/962,465, filed on Jul. 30, 2007.

(51) Int. Cl.
*A61N 1/30* (2006.01)
*A61B 18/18* (2006.01)

(52) U.S. Cl. .............. 604/21; 606/20; 606/22

(58) Field of Classification Search .......... 604/246–256, 604/35, 85, 506, 20–22; 606/20–22
See application file for complete search history.

(56) References Cited

U.S. PATENT DOCUMENTS

| | | | |
|---|---|---|---|
| 3,712,306 A | | 1/1973 | Bryne |
| 3,786,814 A | * | 1/1974 | Armao .............. 606/23 |
| 4,540,404 A | | 9/1985 | Wolvek |
| 5,281,215 A | | 1/1994 | Milder |
| 5,437,673 A | * | 8/1995 | Baust et al. ............ 606/23 |
| 6,033,397 A | | 3/2000 | Laufer et al. |
| 6,283,959 B1 | | 9/2001 | Lalonde et al. |
| 6,494,844 B1 | | 12/2002 | Bladel et al. |
| 6,540,694 B1 | * | 4/2003 | Van Bladel et al. ........... 600/564 |
| 6,551,255 B2 | | 4/2003 | Bladel et al. |
| 6,945,942 B2 | | 9/2005 | Bladel et al. |
| 6,974,463 B2 | | 12/2005 | Magers et al. |
| 7,128,738 B2 | | 10/2006 | Littrup et al. |
| 7,311,672 B2 | | 12/2007 | Bladel et al. |
| 7,402,140 B2 | | 7/2008 | Spero et al. |
| 2005/0222649 A1 | | 10/2005 | Capuano et al. |
| 2006/0282039 A1 | | 12/2006 | Duong et al. |
| 2008/0119838 A1 | | 5/2008 | Vancelette et al. |

FOREIGN PATENT DOCUMENTS

| | | |
|---|---|---|
| WO | WO2008150871 | 12/2008 |
| WO | WO2009018323 | 2/2009 |

OTHER PUBLICATIONS

E.P. Goldberg et al., Intratumoral cancer chemotherapy and immunotherapy: opportunities for non systemic preoperative drug delivery, J. Pharm Pharmacol (2002) pp. 159-180; 54(2).

* cited by examiner

*Primary Examiner* — Kevin C Sirmons
*Assistant Examiner* — Imani Hayman
(74) *Attorney, Agent, or Firm* — McHale & Slavin, P.A.

(57) ABSTRACT

A device and method for safely securing a multilumen device to a tissue, organ or solid tumor within the body of a human during a diagnostic or therapeutic procedure is described. The device is capable of securing the tumor by touching or piercing its surface and providing a coolant to the distal tip. Cooling the tip forms a cryogenically induced region that tightly binds the tip to the tumor, temporarily sealing the entry-track of the instrument. The device further provides at least one injecting/aspirating lumen that can dispense or aspirate a fluid within the tumor. Such construction allows injecting part or whole volume of the tumor while the cryogenically induced bond prevents back-flow of the injected substances through the entry-track.

8 Claims, 5 Drawing Sheets

FLUID FLOWING DEVICE AND METHOD FOR TISSUE DIAGNOSIS OR THERAPY

REFERENCE TO RELATED APPLICATIONS

This application claims the benefit of the filing date of U.S. Provisional Patent Application No. 60/962,465, filed on Jul. 30, 2007, the contents of which are herein incorporated by reference.

FIELD OF THE INVENTION

The present invention relates to fluid delivery devices and methods for delivering direct tissue injection/aspiration to tissue structures within the body. More specifically, the invention relates to a self-anchoring, anti-flow back device capable of securing to a targeted tissue region during diagnostic and/or therapeutic procedures while further providing for optimal injection of compositions to the target tissue structure.

BACKGROUND OF THE INVENTION

Direct deposition of agents interstitially can be of significant beneficial value and is effected by needle or catheter use. Tissue injection has long been a popular, relatively non-invasive means for the direct introduction of various medicaments and other fluids. It is becoming more popular as a means for non-invasive delivery of pharmaceutical preparations of cytotoxic drugs and drug delivery systems into solid tumor because it minimizes tissue trauma, increases local efficacy, and decreases side effects and systemic toxicity. Direct injection, using needles, catheters, or a combined deposition system, is a practical delivery strategy for antiangiogenesis, tumor embolization, hemostasis, and direct cell kill. Direct interstitial chemotherapy is slowly gaining ground among the medical community. A growing number of research papers and clinical reports published during the years 1990-2000 have shown improved efficacy and reduced toxicity in animal as well as in human tumors (E. P. Goldberg et al., *J. Pharm Pharmacol* 54(2):159-180 (2002)).

Most commercial injection systems use needles or catheters which are incapable of preventing backflow of fluid out of the entry-track. These systems suffer from the difficulties associated with lack of a steady means of securing to a target. Current securing and anti backflow injecting systems described in the literature are either too aggressive to tissues or do not insure tight and steady bonding. In addition, injection techniques are operator dependant. Such techniques rely upon perceived tumor margins and mass, subjective assessment of the number of sites of puncture to cover the entire visible mass, and subjective assessment of the liquid-dose fraction to inject at each site. Relying upon commercial needles or catheters, the operator must inject each site with a fraction of the calculated dose at a rate which insures a "homogeneous" distribution and deposition of the agents. In addition, needle tips that do not remain steady during injection results in puncturing or injecting unwanted structures.

Needles used in injection systems most often contain a pointed end having a single orifice. This type of needle does not allow for a controlled distribution of an agent, such as a fluid or a particle, within the interstitial medium of the target. Necrotic zones of the tumor as well as the tumor vasculature should be spared. Therefore, agent distribution within a tumor is random and based on uncontrollable convective forces or on perceived tumor "capacitance" for fluid absorption (subjective fill counter pressure, late visualization of fluid backflow that most often cannot be prevented). Similarly, complete dose administration is not guaranteed since backflow cannot be prevented, is difficult to assess, and intravascular administration is not easy to detect. Multiplying the sites of injection or using multi-needle injectors not only increases the probability of injury to tumor structures but also increases the operation time. Moreover, this type of procedure can lessen a patient's tolerance, leading to decrease in patient compliance to repeated procedures.

Current tissue delivery systems for depositing fluid or fluid-like agents and fluid based substances into an entire lesion utilizes multiple needle tips repeatedly inserted into the tissue in order to increase the diameter of induced necrosis/apoptosis. This approach, however, is both time-consuming and difficult to employ in the clinical setting particularly because multiple overlapping treatments must be performed in a contiguous fashion in order to distribute the agent to the entire lesion. Simultaneous use of multiple needles can reduce the duration of application but is difficult for use in narrow passages or endoscopically since it is technically challenging. The development of pronged injection needle electrodes with multiple arrays should enable the creation of larger foci of more homogeneous fluid distribution with a single penetrating site.

In spite of the promise associated with most techniques of direct interstitial fluid-based therapies such as chemoablation of skin, lung, prostate, breast, head and neck, brain tumors, liver tumors, and the potential clinical applications of these techniques, progress has been hampered by the lack of effective means to achieve the overall objective of efficient and reliable agent delivery to target. One of the most significant shortcomings related to the current systems is the inability to achieve reliable and consistent application from subject to subject. Moreover, insuring full dosage of a therapeutic agent administered to the target lesion can not be guaranteed. Significant sources of this variability are due to differences in the technique and skill level of the operator as well as differing physiological characteristics between patients.

Even if the dose amount of agents injected locally into a tumor tissue is usually much lower than systemic administration, low dosage is desirable in order to prevent side effects. Preventing composition flowing out of the target area is critical, as back flow of the agents can result in unintended harm to healthy structures, create complications, or prolong the procedure. The instantly disclosed system and method has the potential of fast and reliable securing method and more efficient delivery and diffusion of the calculated dose of composition directly into the target tissue through a single injection site, while preventing backflow of injected composition through the entry track of the instrument.

DESCRIPTION OF THE PRIOR ART

The minimally invasive and non-aggressive securing of operative instruments (biopsy, needle, and probe) to tissue using a negative pressure cannula has been described in several U.S patents. U.S. Pat. No. 7,128,738, discloses a system and method of treating fibroadenomas using a minimally invasive cryosurgical procedure. The procedure entails use of a cryoprobe to ablate a fibroadenoma. The cryoablation procedure uses a cryoprobe adapted to perform a period of high power freezing, followed by a period of low power freezing. Such high powered freezing and low powered freezing is followed by a period of thawing, and a repetition of high power freezing and low power freezing, followed by thawing and/or warming of the cryoprobe.

U.S. Pat. No. 6,494,844, and related application U.S. Pat. No. 6,945,942, describe a system and methods for diagnosis and treatment of breast tumors within the breast. The devices include structures which allow a surgeon to secure a mass or tumor within the breast for an extended period of time and for several biopsies, coring procedures, or resections. The tumor is secured to a cannula through the use of a vacuum where a biopsy needle is used to retrieve a tissue. Use of a cryoprobe inserted into the cannula for ablation treatment is disclosed.

U.S. Pat. No. 6,540,694, and related U.S. Pat. Nos. 6,551,255 and 7,311,672, describe devices and methods of use for securing and coring of tumors within the body. The devices include an adhesion probe which secures the tumor to the probe by use of a coolant. The device further includes a coring instrument. Upon securing of the probe to the tumor, a surgeon retrieves a sample by cutting a core sample from the tumor.

U.S. Pat. No. 7,402,140 describes a device for diagnosing tumors. The device includes an adhesion probe which provides securing of a tumor to the probe during surgical procedures by use of coolant. The coolant is directed to the distal tip of the apparatus through a rigid tube, thereby cooling the tip. The device further includes a coring apparatus having a cannula and a means for rotating and translating the cutting cannula.

Although such patents may teach the use of a cryogenic probe for coring and/or cryosurgically ablating a target tissue through the securing cannula none of the prior art teaches an apparatus capable of producing minimal and/or sizeable cryogenically induced regions sufficient to minimize or prevent backflow of injected fluids through an entry track from an associated injection device for fluid-based diagnosis or therapy of a target tissue.

SUMMARY OF THE INVENTION

Given that reliable and consistent application of clinical therapies of direct intratissue injection is highly desirable, the development of improved application systems is well warranted. Such development should include a means for minimizing operator-associated variability, such as procedural safety and efficacy, while providing a means to accommodate the differences in tumor and patient characteristics likely to be encountered during widespread clinical application of fluid-based interstitial therapies used as the sole treatment or in conjunction with loco-regional or systemic therapies.

The present invention is generally characterized by a multilumen catheter including at least one lumen for supply of a cryogenic material wherein the lumen is in fluid connection with at least one cryogenic element effective for lowering at least a portion of the tissue structure in a range near its freezing point. The device also contains at least one lumen for delivery of said treating composition. The multilumen catheter is constructed and arranged for supplying at least one composition to a treatment region within a tissue structure in conjunction with supplying of cryogenic material. Supplying of cryogenic material results in at least one cryogenically induced region formation which is effective to minimize or prevent backflow of the treating composition.

When the apparatus' distal end is immersed into the tissue and the cryoseal is formed, it is possible to inject a composition without creating backflow of the injected composition through the entry track of the apparatus, despite the high hydrostatic pressure that the tissue is under. Under similar circumstances, the current invention further discloses a fluid aspiration element capable of aspirating fluids, or fluid components, from the tissue and/or surrounding area for diagnostic purposes.

A plurality of distal end designs allow for multiple injection/aspiration openings, and/or multiple cooling members. The relative proximal and/or distal location of the openings with respect to the cryoseal may vary dependent upon use within plain or hollow organ.

The composition injection system may include a thermal element for heating or cooling the composition and a metered syringe or pump that allows injecting interstitially, manually or automatically, precisely measured amounts of composition at selected temperature directly into a body tumor or tissue.

The present invention includes a method and apparatus for transient sealing of the entry track of an injection instrument, and securing the instrument into a tissue during fluid-based diagnostic and/or therapeutic applications.

The present invention pertains generally to an apparatus and a method of use to deliver compositions, such as a substance/drug, directly to or into intact or damaged biological tissue, such as normal, benign or malignant tumor, organ, or body structure of an animal or a human. The invention pertains to a cryogenic fluid and composition delivery system and method that allows reversible and/or innocuous adherence of the delivery tip to a tissue target. The invention pertains to a cryogenic fluid and composition delivery system that provides self-adherence, substance injection/infusion into tissue, and prevention of backflow/outflow of injected substances through an entry track of system.

The present invention may use sensors to monitor procedures, such as thermal, bioelectrical, sonic, or photonic sensors. Performance of the method is facilitated by a control system that allows an operator or a technician to deliver and control initiation, growth, maintenance, and regression of the reversible, biologic cryogenic seal. The control system may further be used to manage concurrent positioning of fluid injection openings which allows for a selected amount of substance to be injected into pervious regions of the target tissue or lesion. After entry of these parameters, the system operates automatically to apply cooling to maintain the sealing frozen/unfrozen layer during delivery of compositions to the tissue. The location of the delivery tip as well as injection of compositions may be monitored using imaging devices such as ultrasound, CT, MRI, and sensors, etc.

The present system uses cryogen gas and/or liquid to generate the formation of a frozen/unfrozen layer at the interface between the tissue and the entry track of a diagnostic and/or therapeutic tool that is directly introduced into the target tissue. In the first step, the distal end of the device is guided to the tissue structure using appropriate guiding means. The working end is embedded into a treatment region, such as a tumor, through the tissue surface at a desirable depth and, if necessary, imaged by an external device, such as ultrasound or assessed by sensors. The working end may be made "echogenic" by various known mechanical or chemical coatings, treatments, or alternatively by vibrating it at specific low (sonic) frequencies induced by a driver (COLORMARK and NUVUE COLORMARK, Critical Care Innovations, Inc). Cryogenic fluid is applied to the device, allowing fluid expansion within the lumen at the distal end and providing a cryogenically induced region effective to minimize or prevent back flow. In conjunction with formation of the cryoseal, injection of compositions commences. Formation of the cryoseal is assessed by immobilization of the tip end within the tissue or through measuring means, such as direct measuring of the ring-shaped-to-tissue interface temperature or through calculation by specific software. The cryogenically induced region is left to warm spontaneously or automatically or through guidance of the operator, resulting in melting of the cryoseal as soon as injection is complete or desired. On spontaneous warming, detachment of the device occurs when it becomes movable within the tissue or at a temperature above the tissue freezing temperature.

The present system may further be built into the working end of any delivery instrument of energy, fluid, gas, solid particles, cell, genes, and/or mixtures thereof. The system allows the instrument to secure itself steadily to the tissue and to seal the entry track of the delivery tip of the instrument so that any substance and/or drug injected into the tissue can not flow back and leak out of the entry track, during or after the procedure. In addition, the present invention further provides for injection of the compositions at any location within the target tissue and/or within or near the cryothermal biological seal.

The present system enhances deposition, distribution, and retention of injected compositions into the target tissue, while minimizing the risk of side effects due to under or overdosing, random distribution of substance or leakage of injection fluid into unwanted tissue or structure.

The present system involves using delivery instruments and methods that contact and/or penetrate tissue such as a needle, catheter, probe and the like, whose outer wall may lower the tissue temperature to under its freezing point while providing for internal structure that allows delivery of compositions to the tissue.

Applications involve direct access to superficial normal or tumor (benign or malignant) tissue, to superficial or deep tissue structure or lesion through natural cavity, or open surgery, through skin, or through vascular network, or within endoscope.

The present system and method may be used for fluid-based diagnosis of tissue nature by aspirating tissue fluids or components. A procedure using the system may include a diagnosis step followed by a therapeutic step.

In a preferred method of this invention, the fluid composition injection is set to be effected during the formation of the bonding and occluding of the sizeable frozen/unfrozen layer (cryoseal). It is contemplated within the invention that the cryoseal can be executed first to manipulate the lesion. Injection can be performed after desirable positioning and handling of the lesion. It is also contemplated that injection of the compositions can occur prior to, concurrently with, or after the formation of, during and after the cryoseal to minimize the flow back of injected substance.

It is further contemplated that composition injection openings at the distal end of a needle or catheter tip are distally located with respect to the cooling zone. Alternatively the openings may be proximally located with respect to the cooling zone of the tip. During formation and maintenance of the cryoseal, the compositions are pushed at a distance from the cryoseal, and do not compromise the sealing effect of the cryoseal. It is further contemplated that the fluid injection openings can be positioned anywhere within the target tissue to adjust to various cryoseal shapes, dimensions, various ratios of frozen to unfrozen interfaces, or pervious to impervious interfaces.

It is also contemplated by the invention that a direct tissue injection system and method can be associated with any indicated local, regional and/or systemic therapy.

The invention further relates to an enhanced tissue injection and self-anchoring system that has the potential to lower the dose of substances administered locally. The invention further relates to an apparatus, system and a method that has the potential to reduce the duration of application/operation, reduce the number of injection sites and applications, reduce the total dose administered, and increase the safety and effectiveness of direct fluid-based tissue diagnostic and/or therapeutic procedures.

In accordance with this invention, the term "Cryoseal" is defined as a cooled biological interface layer made of frozen and/or unfrozen target tissue layers that develop about the cooling zone of the device. The cryoseal can be formed in any shape, but preferably ring-shaped, and temporarily prevents fluids from escaping through the entry-track of the delivery instrument to the target tissue and prevents fluids from flowing back through it.

In accordance with this invention, the term "composition" is defined as a substance or mixture of two or more substances, inert or active agents, compositions, such as but not limited to, individual or combinations of free, formulated, or encapsulated drugs, compounds, contrast agents, biologically active peptides, genes, gene vectors, proteins, or cells for therapy, into the tissues or cells of a human or animal patient. The active agents, include but are not limited to, saline solution, heating or cooling fluids, photosensitizer, radiosensitizer, radioisotopes, sclerosants (sclerosing agent), radio-seeds, thermoseeds, glue, vaccines, genes, immunologic factors, hormones, particles, nano-particles, and combinations/formulations thereof.

It is contemplated that for the purpose of tissue kill, compositions that act directly on cells and/or indirectly on tissue structure and more particularly on their vascular bed would be best suited. Although direct intralesional therapy is well suited for injection of a fluid composition it will be understood by those skilled in the art that other compositions, such as, for example, viscous compounds, semi-fluids, or solids in granular or powdered form may also be injectable. Furthermore, the compositions may be injected in a liquid state and, after injection, solidify under the influence of body heat or by the application of an external energy source, such as, for example, microwave, radio frequency or electromagnetic energy. Alternatively, a solid or semisolid composition may be injected, and, after injection, liquefy under the influence of body heat or an external energy source.

As used herein with reference to supplying at least one composition to a treatment region within the tissue structure, "in conjunction with" is defined to include injection of the compositions prior to, subsequent to, or concurrently with supplying of cryogenic material.

In accordance with this invention, the term "liquid refrigerant and refrigeration system," "cryogenic material," "cryogenic fluid," and "cryogenic agents" are used interchangeably and refer to the coolant for the system and/or the system itself (i.e. tubing, containers, connectors, control systems and interconnections thereof). The coolant is defined and may be a mixture of one or more coolants at high or low pressure. Cryogenic materials include, but are not limited to, chloroform, ether, fluorocarbon refrigerant R134, liquid air, liquid argon, liquid butane, liquid carbon dioxide, liquid DYMEL blend, liquid helium, liquid nitrogen, liquid oxygen, liquid propane, liquid refrigerant compounds and other coolant formulation known from those who are expert in the art. Preferred refrigerant for the system may be R134 or liquid $CO_2$, from any kind of cylinder or cartridge. The cylinder or cartridge can be either disposable or re-usable. Alternatively, cryogenic materials may be cooled saline at low temperature flowing through a pump-flow regulator system. Consumption of the coolant is minimal and cooling principles used are simple such as change of phase or gas expansion, requiring low cost manufacturing and allowing for disposable single use injector. Added advantages of using low-pressure gas coolant include is lack of need for costly materials or high complexity of testing for safety systems which required for high-pressure gas operated systems.

In accordance with this invention, "Fluid-based diagnosis" is defined as injection of a fluid that allows discrimination and determination of the tissue nature and characteristics or aspiration of tissue fluid components, including cells or tissue structures, for analysis.

Accordingly, it is a primary objective of the instant invention to provide a system and method for diagnosing and/or treating target tissues, particularly solid tumors, by aspirating and/or injecting a composition into the target tissue.

It is a further objective of the instant invention to provide a device and a method for treating target tissues by injecting a composition while minimizing exposure of healthy tissue to the composition.

It is yet another objective of the instant invention to provide an apparatus with low profile design and smooth surface to penetrate tissue with minimal tissue trauma.

It is a still further objective of the invention to provide an apparatus with tissue anchoring and securing cryogenic means before, during and/or after injection resulting in easier, faster injection procedures, less risk of unwanted displacement of an indwelling instrument, and minimal risk of injection of composition to non-targeted tissue structures.

It is another object of the invention to provide an apparatus with cryogenic means for stabilization and steadiness before, during and/or after aspiration resulting in improved aspiration procedures, less risk of unwanted displacement of an indwelling instrument, and minimal risk of procedural complications.

It is another object of the invention to provide an apparatus with means to prevent backflow of injected composition along the tissue entry track of the instrument.

It is another object of the invention to provide an apparatus with means to inject and prevent back flow of a composition through a single entry track and prevent back flow of composition while using the entry track for injection to minimize trauma to the tissue.

It is another object of the invention to provide an apparatus with means to inject and prevent back flow of a composition through a single entry track and prevent back flow of composition while injecting the necessary dose of composition within low compliant target and/or against naturally or artificially elevated interstitial target tissue pressure.

It is another object of the invention to provide an apparatus with means to prevent back flow of fluid from tissue in combination with a means to accommodate various instruments for diagnostic or therapeutic purpose, including interstitial fluid injection/aspiration therapies and/or interstitial energy-based devices, such as thermal, sonic, light ablation, or electroporation.

It is another object of the invention to provide an apparatus with high or low-pressure refrigerant means so that construction is simplified, cost is reasonable and procedural risks are minimized.

Other objects and advantages of this invention will become apparent from the following description taken in conjunction with any accompanying drawings wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Methods, systems, and apparatus according to the present invention rely on placement and use of one or more anchoring and injection/aspiration elements positioned at or within a treatment region of a patient. The treatment region may be located anywhere in the body where fluid injection/aspiration may be beneficial. Most commonly, the treatment region will comprise a solid tumor within an organ of the body, such as the liver, kidney, lung, bowel, stomach, pancreas, breast, prostate, uterus, muscle, brain. The volume of fluid-based substance to be injected depends on the size of the tumor or other lesion, typically having a total volume from 1 cm.$^3$ to 150 cm.$^3$, usually from 1 cm.$^3$ to 50 cm.$^3$, and often from 2 cm.$^3$ to 35 cm.$^3$. The peripheral dimensions of the treatment region may be regular, e.g. spherical or ellipsoidal. However, typical tumor shape is irregular. The treatment region may be identified using conventional imaging techniques capable of elucidating a target tissue, e.g. tumor tissue, such as ultrasonic scanning, magnetic resonance imaging (MRI), computer-assisted tomography (CAT), fluoroscopy, nuclear scanning (using radio labeled tumor-specific probes), and the like. High-resolution ultrasound or CT can be employed to monitor the size and location of the tumor or other lesion being treated, intraoperatively or externally.

The treatment region may also be identified with sensors for sensing tissue parameters such as electrical impedance, temperature, pressure, and optical characteristics disposed at the distal end of the indwelling self-anchoring catheter on injection/aspiration needle. One or more sensors may be used in any desirable combination and disposition over the indwelling end of the self-anchoring catheter or needle.

In an illustrative embodiment, the present invention generally provides a tissue-anchoring, fluid delivery and aspiration system, and preferably a fluid delivery system for delivering cytotoxic drugs to the interstitial space of solid tumor tissue. While the system can be used for a variety of purposes, it is preferably used to treat soft tissue tumors under ultrasound guidance in order to minimize exposure to radiation and reduce cost associated with the procedure. Although the preferred embodiment describes a catheter-like device, it is contemplated within the invention that the features described apply to needle, cannulas, and other needle-like devices.

Figures 1A, 1B:
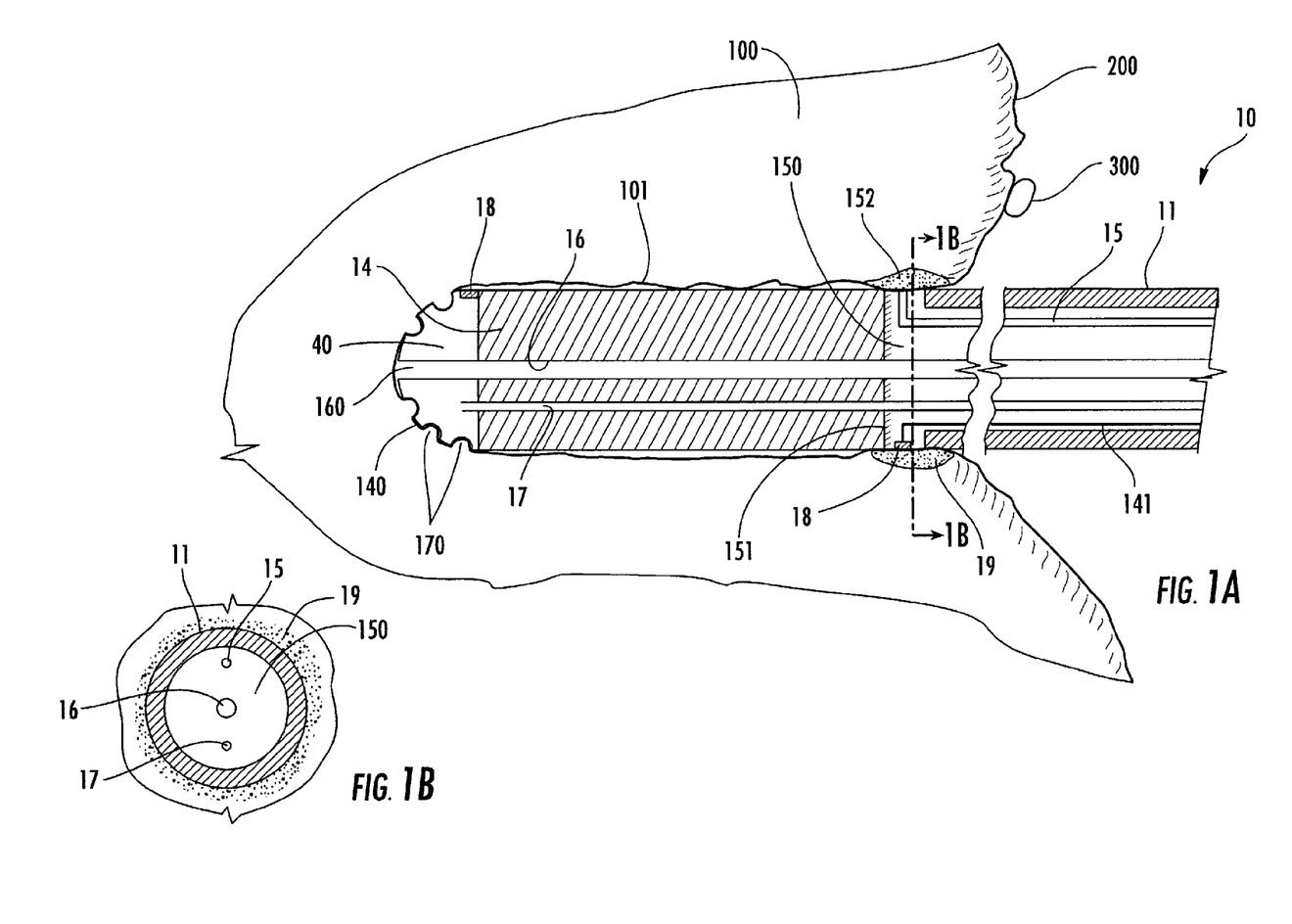
FIG. 1A is a longitudinal sectional view of the distal end of the catheter element embedded into the treatment region of a tissue structure.
FIG. 1B is a cross section taken along the line 1B-1B of FIG. 1.
Figure 3:
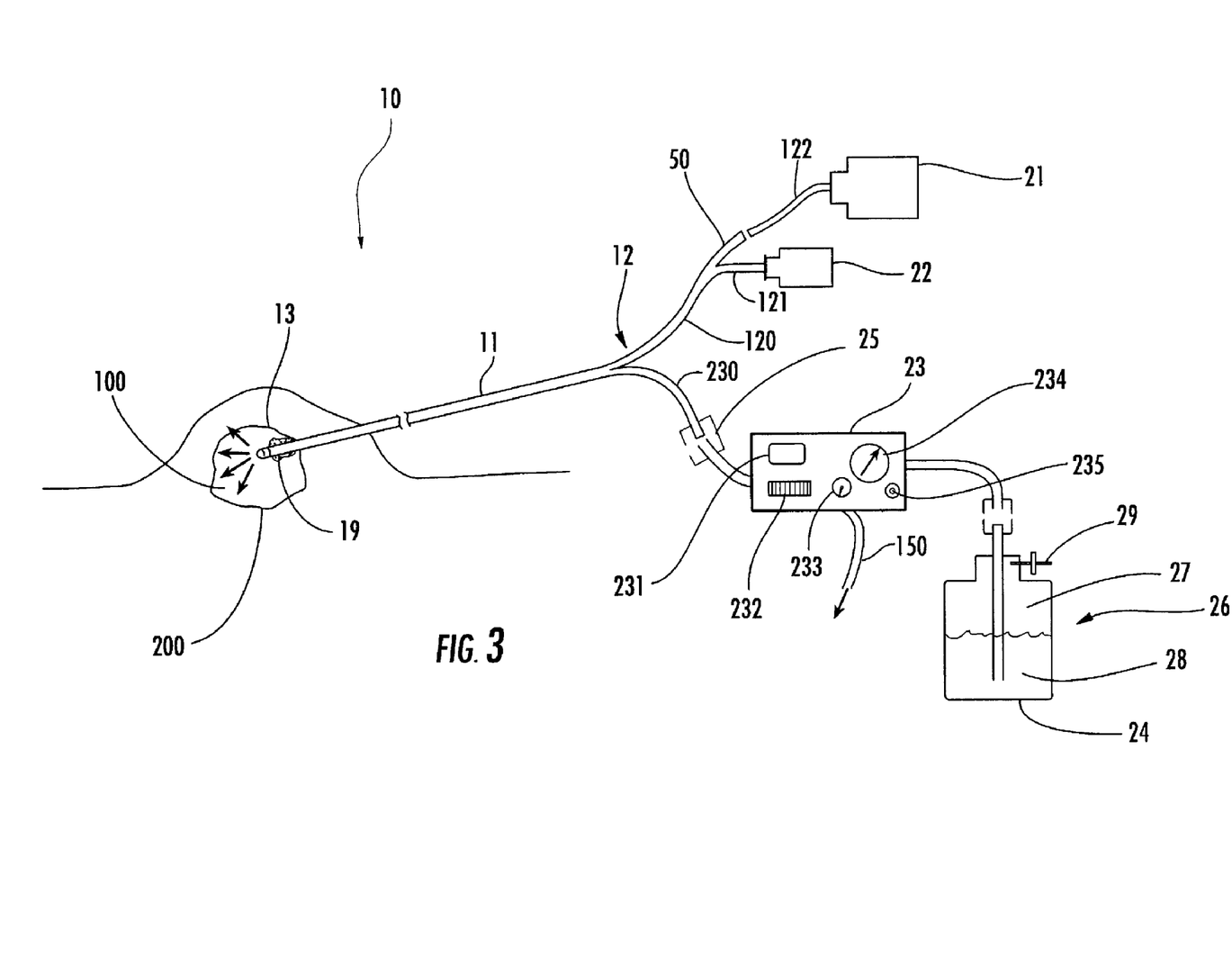
FIG. 3 is a perspective view of a self-anchoring and injection/aspiration system for delivering a treatment composition to a tissue structure, in accordance with an embodiment of the invention.

As illustrated in FIGS. 1A and 3, the self-anchoring, backflow limiting device includes a multilumen catheter member 10. Multilumen catheter 10 has a proximal end 12, a distal end 13, an inner lumen 150 extending through, and a cryogenically induced region (or anchoring member) 19. At least one cryogenically induced region and injection lumen includes a means for occlusion of the instrument entry track into the tissue and an injection opening 160 located at or distal to the cryogenically induced region. The multilumen catheter is comprised of a shaft 11. Inner lumen 150 of the multilumen catheter 10 has adjacent multiple lumens (15, 16, 17) as illustrated by FIGS. 1A and 1B.

The distal end 13 of catheter member 10 and/or the cryogenically induced region inner and/or outer wall 140 is optionally equipped with sensing members 18. Sensor members 18 are electrically coupled to a data logger (not represented), a controller, and monitoring system (not represented). The catheter 10 has fluid control means (aspiration, injection) at the proximal end 12 through tubing 120, and cryogenic fluid control means with controller 23 through tubing 230.

Quick connectors at proximal ends of tubing 120 and 230 allow for an instant disconnection of the catheter member that is readily interchangeable and may be provided as a disposable element of the invention. The distal end 13 of the catheter 10 may be steerable by conventional means. Alternatively, the distal end may be of a flexibility, toughness, and formability differing from that of shaft 11. The tip end 14 is preferably closed, blunt or tapered or round, but may be of any desirable shape, flexibility and openness like pointed, sharp, cutting, fully open, pre-bent, or bendable, and/or steerable. Such metal as stainless steel, titanium, platinum or metallic alloy, or memory material like nitinol may be used for its structure. Tip 14, or a portion thereof, may also be constructed of any material, such as but not limited to radio opaque material, capable of being used for radiography or fluoroscopy purposes. Any desirable combination of toughness, slidability, or flexibility and other desirable characteristics for the proximal end 12 and distal end 13 of catheter 10 is within the spirit of the invention. Proximal end 12 has two extension members 120 and 230; extension member 120 comprises two separate tubings 121 and 122, see FIG. 3. Tubing 122 is coupled to inner lumen 17 of catheter 10 and more particularly to inner lumen 40 which fluidly communicates with opening ports 170 located at distal end 13 of catheter tip end 14. Tubing 121 fluidly communicates with inner lumen 16. Lumen 16 is in fluid communication with opening port 160 at tip end 14.

Opening ports 160 and 170 are located distal to or at the level of the cryogenically induced region or anywhere along tip of distal end to allow for desirable injection-aspiration patterns. Opening ports 160 and 170 may be located proximal to an cryogenically induced region when distal end 13 comprises more than one cryogenically induced region As illustrated in FIG. 3, the proximal end of tubing 121 is connected to a pressurized fluid source 22, for instances a syringe or a pump (not represented) well known to one of ordinary skill in the field. The pressurized fluid source provides a means to inject, at a controlled rate and pressure, at least one fluid (composition and/or tissue fluid) of interest.

FIG. 3 also illustrates the proximal end of tubing 122 connections to a vacuum source 21, for instances a syringe or a pump (not represented) well known to one of ordinary skill in the field. The vacuum source provides means to aspirate, at a controlled rate and pressure, at least one fluid (composition and/or tissue fluid) of interest.

It is contemplated that tubing 121, 122 and openings ports 160, 170 can be used interchangeably as injection and/or aspiration members if they are connected to the corresponding vacuum and pressurized sources that can be used sequentially or simultaneously through a manifold 50 (see FIG. 3). For instances, a 4-way manifold (not detailed here) could allow for a multiplicity of operations, including but not limited to aspirating fluids and waste, injecting, separately or in conjunction, composition and/or other desirable agents, such as but not limited to contrast medium, hot or cold fluids, sealing substances. Moreover, a single tubing can be used as an injection and aspiration means.

Figure 2:
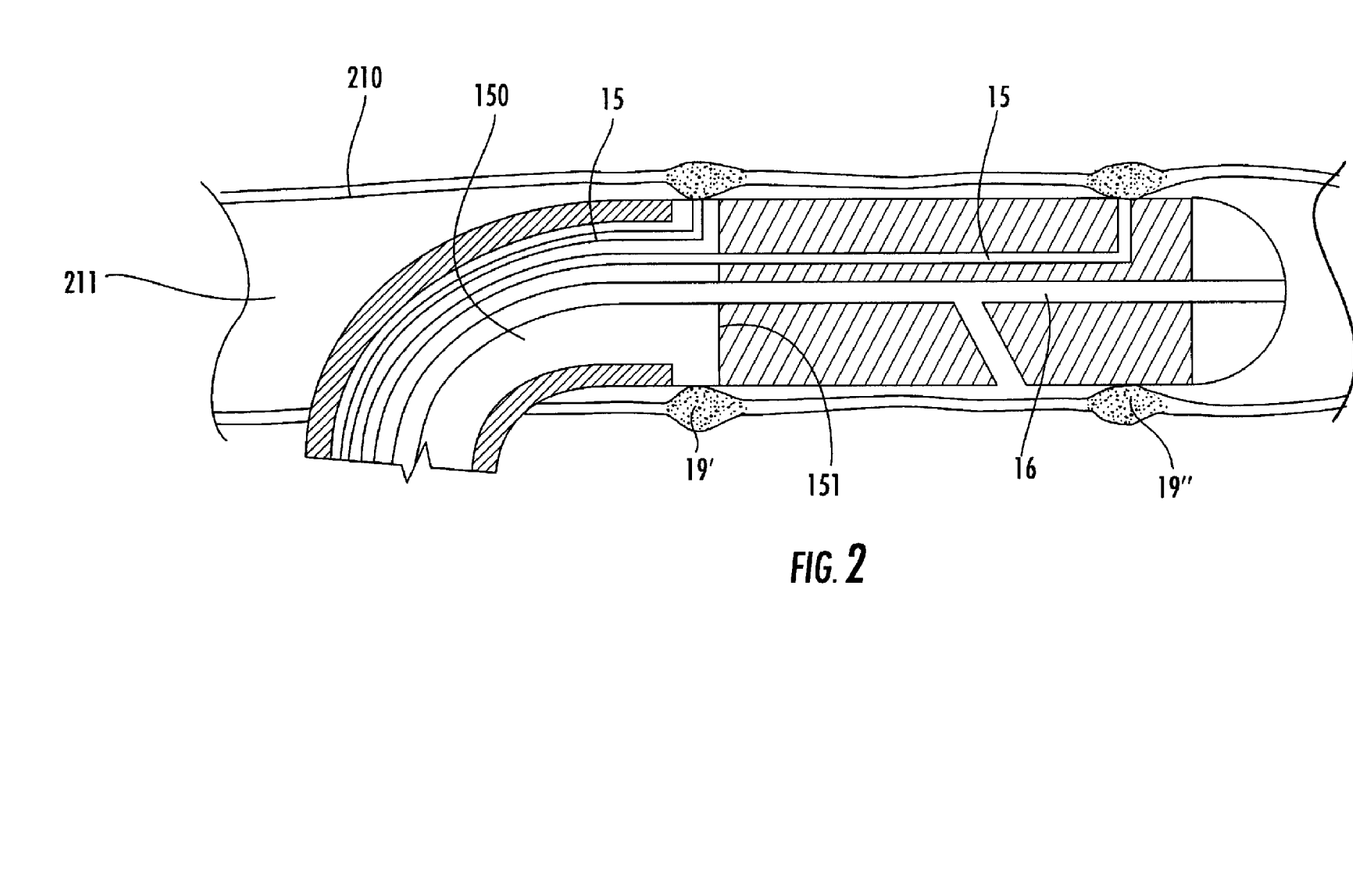
FIG. 2 is an alternative embodiment of the invention, illustrating formation of multiple cryogenically induced regions that delineate a region for deposition, diffusion, and retention of injected compositions within a hollow organ.

FIG. 2 illustrates an alternative embodiment of the invention. In addition to tumors, the multilumen catheter can also be used to treat areas of the body such as a vascular or organ lumen. As illustrated, the multilumen catheter is percutaneously introduced into vein lumen 211 through vein wall 210. As further depicted, the multilumen catheter has two cryogenically induced regions 19' and 19". Injection of a treatment composition, such as, but not limited to a sclerosant, is accomplished through lumen 16. The formation of the two cryogenically induced regions allows the substance to remain at the site of deposition without being diluted or washed out by blood flow. Although the tip 14 is illustrated as being closed, it is within the invention that the tip also includes one or more openings. The formation of each cryoseal can be phased to alternate with each other. Percutaneous approach and vascular access is made easier with the adjunct of the echogenic enhancement of the vibrating driver (COLORMARK & NUVUE COLORMARK, Critical Care Innovations, Inc).

Figure 4A:
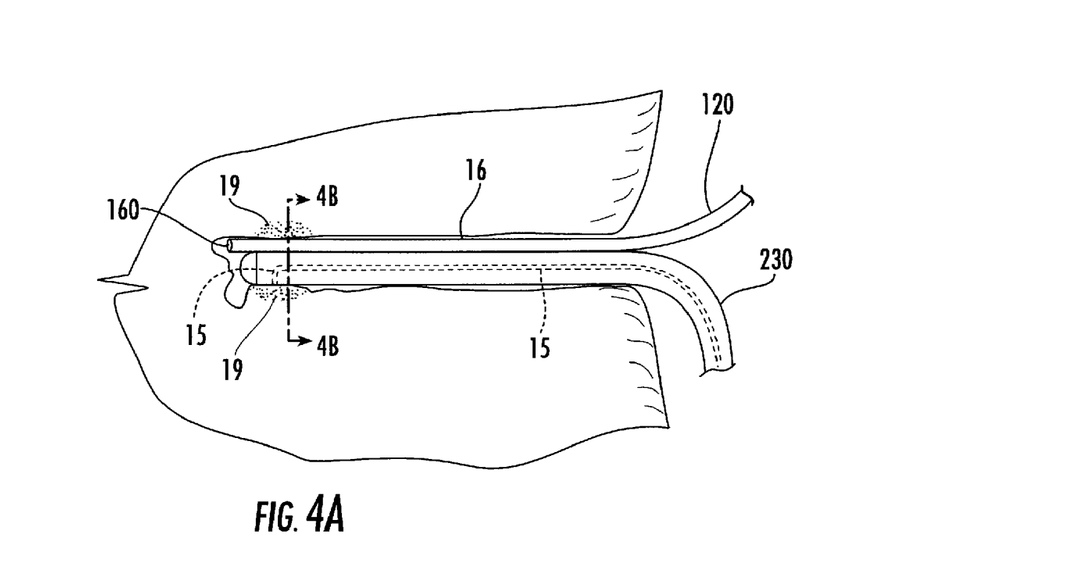
FIG. 4A is an embodiment of the multilumen catheter, illustrating one lumen in slidable connection with the outer surface of the catheter and in parallel relationship with the lumen in fluid connection with a cryogenic element.
Figure 4B:
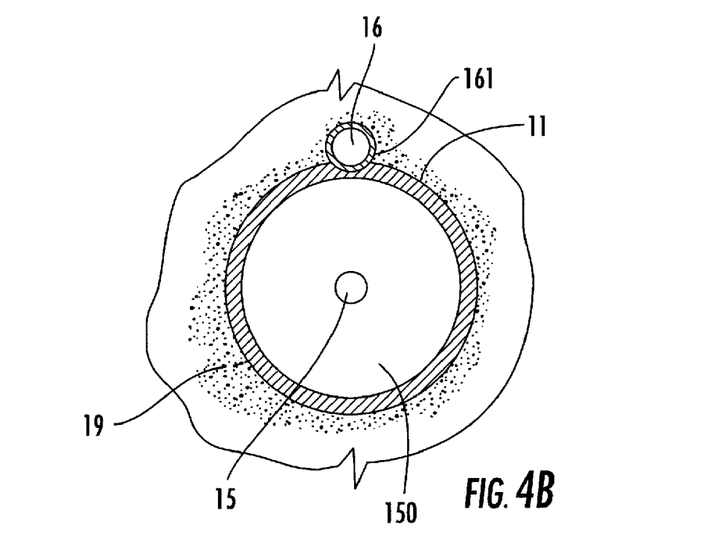
FIG. 4B is a cross section taken along the line 4B-4B of FIG. 4A.

FIG. 4A illustrates another alternative embodiment of the invention, comprising a single tubing 16 and distal end opening 160, similar to that of FIG. 1, along with a single cryogenically induced region 19 proximal to opening 160. FIGS. 4A and 4B show injecting lumen 16 located parallel and adjacent and in slidable contact or arrangement with the outer wall surface of catheter shaft 11 and distal end 13. Distal end opening 160 of lumen 16 is represented protruding off the distal end of tip 14, illustrating a means for adjusting depth of immersion of distal end of injection/aspiration tubing 16 out of sliding channel 161.

The cryogenic element of the invention includes one or more cryogenic elements of the invention which plays a role in providing the cooling effect associated with the anti-flow back cryogenically induced region. As depicted in FIG. 3, extension member 230 of proximal end 12 communicates with lumen 15 and 150 of distal end 13. Lumen 15 provides cryogenic fluid at high or low pressure to chamber lumen 150 whose bottom defines level of wall 140 cooling zone and location of cryogenically induced region interface (frozen/unfrozen layer). The location of bottom wall 151 of chamber 150 defines the level, dimension and shape of cryogenically induced region, thus resulting ranges of size and shape. The location of cryogenically induced region defines the length of working member of catheter distal end 13.

Optional conduit 141 runs along shaft longitudinal axis within wall thickness of shaft 11 and may couple sensors (thermal, pressure, impedance) 18 with signal data loggers (not represented) through electrical wires, optical fibers, or any coupling cable for signal transmission known to the field.

Extension member 230 is connected with a quick pneumatic/electric connector 25 to controller 23 and to a cryogenic source gas cylinder 24. Although the cryogenic source 26 is illustrated as having a gas phase 27 and liquid phase 28, any liquid refrigerant and refrigerant system is contemplated for use within the invention. Gas cylinder 24 may contain a cylinder valve 29.

Controller 23 contains modules for converting signals from sensors into readable parameters, such as, but not limited to, temperature or resistivity of cooling zone and tissue interface, for monitoring and controlling operation of catheter. Controller may include indicators for temperature indicator 231, timer 232 and/or setting for cryoseal duration, pressure regulator 233, pressure gauge 234, power switch 235. Parameters can be displayed on a controller screen and/or on a separate display screen such as a computer using specific software. Controller may also display anchoring member temperature, time, initiation or termination of anchoring, pressure within cryogenic tubing. Although depicted near controller 23, gas outlet 150 may be located in other areas.

Figures 5A, 5B:
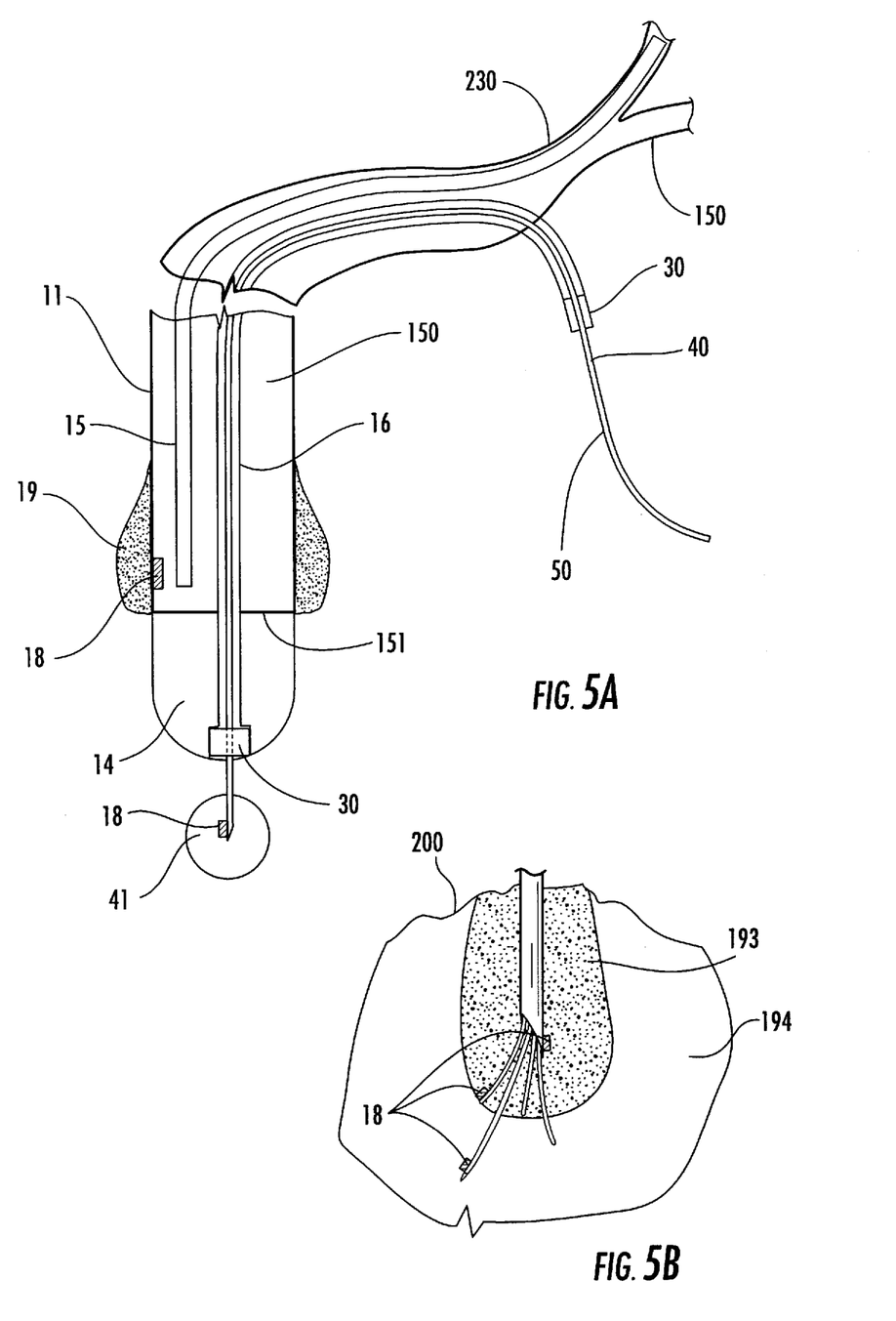
FIG. 5A is a longitudinal section of a self-anchoring cannula whose operative channel accommodates various applicator(s) or guide(s).
FIG. 5B is an expanded view of the distal portion of the catheter as exemplified in FIG. 5A, illustrating multiple, variable length applicators.

In another illustrative embodiment of the invention, FIG. 5A depicts a self-anchoring cannula where channel 16 is an operative channel that accommodates and allows various sliding applicators or guides 41 for cannula guidance and/or tissue operation. The cannula tip end 14 comprises the distal lumen opening 160, which is equipped with a valve 30. Valve 30 may be a haemostatic valve or be constructed of self-sealing silicone plug. Any other sealing material which can be used as a plug is contemplated within the invention. The plug seals the cannula distal end against hydrostatic pressure, but allows passage of a needle, probe, balloon catheter or any tissue operative instrument known to those in the art, by way of a slit, for operation. Plug seal 30 resiliently closes after removal of instrument. Facultative plug or haemostatic valve 30 may be located at proximal and/or distal end of lumen 16.

FIG. 5B is a magnification of 41 and illustrates the multi-needle slidable applicator protruding off anchoring tip 14 which is deployed in operative mode for a better distribution of injectable composition. The applicators are constructed and designed to be variable in length as well as being capable of being deployable in situ. Tip end applicators 41 are optionally equipped with sensors 18 and can be used to provide energy sources, fluids, mechanical devices, guide wires, or the like, to the tissue. It is contemplated that injection and/or aspiration lumen, such as illustrated in FIG. 1, would add functionality to the anchoring cannula. It is also within the spirit of the invention that retractable, adjustable length, and deployable fluid, balloon catheter or needle, energy and/or operating tip ends and/or mechanical devices may be used in conjunction with any of the devices embodied within the invention. In a non-limiting illustrated example, FIG. 5B depicts applicators which are variable in length. Several of the applicators are positioned within frozen margin of a seal 193 while several other applicators are illustrated as extending to unfrozen region 194.

The catheter and lumen are made of plastic, and or composite materials that are compatible with critical parameters such as pressure, profile, yield, and compatibility with composition, pushability, flexibility, kink and torque resistance, sterilization and the like. They should also be able to incorporate wires and microcomponents such as sensors or optical systems. A number of materials are available for catheter and thin wall miniature tubing construction, including, but not limited to, polyethylene (PET), nylon, PE (cross linked and other polyolefin), polyurethane, polyvinyl chloride (PVC), and composite-like materials (polyamide/polyurethane composite), polyurethane TECO polymers, poly(tetrafluoroethane) or poly(tetrafluoroethylene) (PTFE), PEBAX, HYTREL, polyimide, and braided polyimide.

Size of catheter or needle: The outer diameter of the shaft 11 could range in size, for example, from 0.3 mm for microprocedures, to 2.5 mm for endoscopic procedures, to 10 mm or more for open surgery procedure or direct procedures through natural openings or surgical cavities. The length of the shaft depending on the location of tissue from the body surface could be in the range of, for example, 15 cm for easily accessible tissue such as the prostate gland to 130 cm or up to 200 cm for endoscopic procedure to distal lesion of the aerial, or digestive tract. In a needle injector embodiment of FIG. 4A, the cooling zone was determined to have a height of 70 mm, diameter of cooling tip of Fr.3, diameter of adjacent slidable metal needle of 24 G, and diameter of adjacent thermocouple TEFLON wire of 1 mm. All three parts were in close contact with each other within a PTFE sheath of 2.7 mm diameter. Using this prototype inserted into a chicken leg, a digital thermometer Fluke 54II (Fluke, USA), and a tissue biocompatible marker (SPOT, GI Supply, Inc, USA), injection procedure was effected at slightly negative temperature (−3° C.) of the ring-shaped cryoseal to tissue interface, even though freezing point of SPOT is 0° C. Cryogen was $CO_2$ from a high-pressure cylinder. Warming was spontaneous.

In the catheter injector embodiment of FIG. 4A, diameter of distal cooling tip was Fr.8 and height of 10 mm. The injecting tip opening was at a level of the cooling tip distal end with the metal injecting tubing at 24 G. Injection procedure was possible during warming of indwelling catheter injector when wall temperature was slightly positive (start+3° C.) and maintained at that level during the rest of the SPOT marker injection. No backflow of the marker though the entry-track of the catheter was detected when the cryoseal was "on." Control tests indicated that backflow was present during injection in the absence of the cryoseal. There was no need for injection opening of adjacent injection tubing 16 of FIG. 4A to be protruding for injection to be successful, complete, and without backflow.

Proximal end of operative channel 16 of FIG. 5A may be equipped with a means to control the depth of penetration of distal end tip 14 and injection tip end 41. First cannula shaft and injection stem may bear markings at known distances, and second valve 30 allows for sliding and adjusting depth of penetration of injection stem off the cannula indwelling end. It is obvious that during positioning of the catheter, needle or cannula equipped with the retractable inner needle instrument or device, the inner instrument or device remains retracted during positioning and securing of the cannula to the target, which are then deployed in operative position.

Critical dimensions of the cryoseal: the frozen and/or unfrozen ring-like shaped tissue layer created longitudinally and radially along the instrument axis and about the cooling zone 152 of injector distal end 14 may vary in size and shape with the thermal field created about the cooling zone. Its height may vary from 0.5 mm to 50 mm, preferably from 1 mm to 30 mm, and more preferably from 5 mm to 10 mm. Its thickness temperature and structure (among other physicochemical parameters) may also vary with cooling temperature and duration of application. However, cryothermal and structural change expansion (thickness) into tissue is controllable so that only the anti-backflow and/or the anchoring effect are obtained without any damage or harm to surrounding tissue. Alternatively lower negative temperatures for the cryoseal or longer duration or activation to the lower temperatures may entail the growth of large, sizeable frozen/unfrozen volumes. If it is estimated that the indwelling part of the catheter has created an irregular and large entry track, the operator may form a larger frozen ring than otherwise would be necessary. However, the preliminary injection of inert contacting fluid, such as isotonic saline liquid, into an irregular entry track through injection openings may circumvent the issue and allow for creation of a small self-adjusted fluid-to-tissue biological cryoseal.

Although the cryoseal is made of structured water and tissue components at various temperatures that seal and bond the indwelling cooling wall of fixed dimensions to the tissue, the cooling zone of wall 152 may be sizeable. For instance, such cooling zone may be that of an inflatable cooling balloon whose interior connects to lumen 15 through a wall opening for the cryogen, and to lumen 150 through a cryogen return opening. Although the tip end of device 11 is usually cylindrical and straight any other shape best suited for the intended use, such as such as pigtail, bent, or curved shape is within the scope of this invention.

A typical mode of operation, such as for percutaneous image-guided solid tumor tissue injection, utilizing the catheter/needle of the instant invention is as follows:

Tumor characteristics, such as location, shape, structure, relation to structures or organs, are determined prior to injection so that the guidance technique, the needle path, the type and volume of composition to be injected are precisely calculated. The composition is prepared and ready to use for the indicated procedure.

In the first step, the distal end of the device is guided to tumor site (FIG. 1) with appropriate guiding means. A preferred, but non-limiting means includes imaging guidance using Ultrasound with an enhanced echogenicity device using COLORMARK or NUVUE COLORMARK features (Critical Care Innovations, Inc).

In the second step, the distal end is embedded into tumor tissue 100 through tissue surface 200 at desirable depth and if necessary imaged by an external device 300 such as ultrasound, or assessed by sensors 18.

The third step of the procedure provides for opening of the cryogenic fluid valve of controller 23 (manual switch, pedal, automated switch) to allow fluid circulation and/or expansion within lumen 150. This results in cool down of the wall of indwelling part of injector and creates a cooled ring-like zone made of frozen/unfrozen tissue as the wall temperature drops down to the freezing point temperature of the tumor, i.e. in the range of about +4 degrees C. (° C.) to −4° C. or lower, preferably 0° C. to −4° C., or lower. Given that a thin layer of unfrozen/frozen tissue suffices to create a tight and leak proof bond at the multilumen/tissue interface, there is no need to make a large frozen cryoseal ring when the goal is only to perform an injection or aspiration procedure.

The cryogenically induced region is maintained by adjusting the flow of the cryogenic fluid over time so that the cryogenic seal/bond thickness is sustained. The temperature of the wall to seal interface bond is regulated to desirable wall device temperature for flowing substances (or substance mixture) to the distal end of the injection lumen (i.e. temperature is slightly higher than freezing point of substance, or freezing point of substance is slightly lower than that of tissue). Substance can also be mixed with low freezing point fluids.

The fourth step includes injection of the composition. Injection commences in conjunction with cryoseal formation and is assessed either by immobilization of the tip end or ring/tissue temperature measured or calculated by specific dedicated software, such strength may vary with the nature and hydration of the target tissue. Injection may be effected during re-warming of the cryoseal and melting of ice crystals, as long as the bond temperature is still strong enough to insure sealing of entry track 101 of indwelling multilumen catheter 12.

Depending on tissue characteristics, indication, volume to be injected, patient cooperation and clinical status, injection may be effected at once and quickly against tissue pressure, lasting only a few seconds, from 1 to 10 seconds. Injection may be effected slowly at low pressure over a period of seconds to minutes. Injection may last over longer periods if necessary. In any case, the cryoseal is maintained at stable and desirable size for the desirable duration by monitoring and controlling its temperature with cooling/warming (spontaneous or artificially controlled) sequences. Sequences are based on "on" and "off" position of cryogenic fluid valve, continuous supply of cryogen at different pressure, or combination of both, or on any other means known by those of skill in the art.

Injection sites: Injection can be performed within warm, cooled, and/or frozen tissue, since the device design allows for adjusting the location of injection openings in relation to tumor characteristics and/or thermal fields. Unlimited injections may be executed within pervious tissue structures and be concurrent to a static or a dynamic cryoseal, i.e., a steady, growing or regressing. It is understood that a previously impervious structure of the cryoseal may be injected with composition when returning to a state of fluid permeability.

In the fifth step, the cryogenically induced region is left to warm and/or melt spontaneously or automatically. The cryoseal may melt as soon as the injection is completed. Upon spontaneous warming, detachment occurs when the device becomes movable within the tissue or its temperature is above its freezing point. It may be desirable to dislodge and remove the device from the tissue before full melting of the cryoseal. In such a case, warming of the cooling zone may be effected by heating resistance located in the wall of shaft 11, or by closing a valve located on return lumen 150. Such action prevents further cryogen expansion and permits warm cryogen fluid into lumen 150. If fractionation of dose or multiple injection sites are a preferred mode of administration, steps 2 to 4 are repeated. If a period is estimated necessary for administered dose to be distributed or absorbed within target tumor, the cryoseal is maintained for such desirable period without further injection.

It is further contemplated that the cryogenic fluid flow can be short in duration, alternated with stop flow periods of cool-warm cycles, or continuous over variable duration periods to allow for permanent securing and positioning of the fluid flow device to the target tissue. It is also contemplated that a sizeable cryogenic seal may have a fluid impervious structure and/or a damaging structure and/or a damaging structure for tissue cells or components. By adjusting the temperature (for instances with low boiling point coolant) and duration of the cooling/warming cycle and performing one or multiple cycles the deleterious effects of the cryoseal can be associated with the physicochemical effects of the injected fluid-based composition.

Termination of the cryogenically induced region occurs by preventing cryogenic fluid admission, and melting cryogenic seal to allow for fast detachment of fluid flow device. At termination, the device can be retrieved from the tissue.

Permanent seal of entry track: it may be desirable to permanently occlude the entry-track of the device after removal. In such case injection lumen 16 allows for injecting tissue with sealing agents, such as but not limited to glue or fibrin glue, during removal of the device. Some sealing agents may be selected from substances that are liquid in cold state and solid in warm state.

Aspiration mode: operator effects step 1 to 3, then aspirates tissue fluids and or tissue components through the opening 170 of lumen 17, by way of a mechanism including, but not limited to applying negative pressure at the proximate end of the aspiration lumen.

Tissue washing mode: operator effects steps 1 to 3, then injects compositions and simultaneously or sequentially aspirates tissue fragments, debris, cells, and fluids.

Alternative use of self-anchoring injector: an alternative use of the injector of the invention includes manipulation of the tissue of interest before or during treatment administration such as but not limited to techniques of imaging, ablation, injection, or extirpation.

Tissue Ablation. In addition to methods for creating a self-anchoring, it is contemplated that the anti-flow back device which is capable of injecting compositions into a treatment site can further be used for tissue ablation methods. Such tissue ablation techniques may include cryogenics and/or injection of various ablation compositions, such as free drug-solutions or carrier bound drugs.

The apparatus of the invention can be combined with any open access and/or minimally invasive ablation techniques (high intensity focused ablation (HIFU), microwave, laser light, radiofrequency (RF), cryosurgery, brachytherapy), or loco-regional therapies (embolization, chemoembolization and the like), or systemic therapies (chemotherapies).

All patents and publications mentioned in this specification are indicative of the levels of those skilled in the art to which the invention pertains. All patents and publications are herein incorporated by reference to the same extent as if each individual publication was specifically and individually indicated to be incorporated by reference.

It is to be understood that while a certain form of the invention is illustrated, it is not to be limited to the specific form or arrangement herein described and shown. It will be apparent to those skilled in the art that various changes may be made without departing from the scope of the invention and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A process for controllably delivering a treating composition to a tissue structure along an entry track comprising:
   providing a backflow limiting device, said device having a multilumen catheter including at least one first lumen to provide at least one cryoseal about a catheter-tissue interface at a distance from an injection site, said cryoseal sized and shaped to seal said catheter to said tissue structure, said first lumen in fluid connection with at least one cryogenic source effective for lowering at least a portion of said tissue structure to a temperature within the range of at or about a tissue freezing point to form said cryoseal, and at least one second lumen in fluid communication with a treating composition delivery source and having a delivery end for providing at least one treating composition to an interstitial space within said tissue structure, said delivery end positioned a distance from said cryoseal to allow administration of said at least one treating composition to said tissue at a location which is distal from said cryoseal;
   said multilumen catheter being constructed and arranged for injecting said at least one composition to a treatment region within said tissue structure prior to, subsequent to, or concurrently with formation of said cryoseal;
   positioning said backflow limiting device within or proximate to said tissue treatment region;
   securing said backflow limiting device to said tissue structure by delivering cryogenic agent to a portion of said multilumen catheter lumen, whereby at least one cryoseal is formed proximal to a point of delivery of said treating composition and which is effective to minimize or prevent backflow of said treating composition;
   maintaining said cryoseal; and
   delivering said treating composition to said treatment region within said tissue structure by injection;
   whereby backflow of said treating composition through the entry track is prevented.

2. The process according to claim 1 wherein said treatment site is a benign or malignant tumor, or a dysfunctional zone of an organ or target tissue.

3. The process according to claim 2 further includes identifying said treatment site by using sensors for sensing tissue parameters selected from the group consisting of electrical impedance, temperature, pressure, optical characteristics, and combinations thereof.

4. The process of claim 3 whereby tissue fluids, cells or other compositions are aspirated from said tissue structure.

5. The process according to claim 1 further including a step of providing cooling and deposition of the composition to said treatment region effective for killing said tissue.

6. The step of ablating according to claim 5 further comprising two or more repeated cooling and freezing cycles alternating with warming periods.

7. The process according to claim 1 wherein said step of securing said backflow limiting device to said tissue structure by delivering said cryogenic agent to the portion of said multilumen catheter lumen further includes the formation of at least one cryoseal distal to said point of delivery of said treating composition.

8. The process according to claim 1 wherein said cryoseal forms a ring-shaped structure of frozen and unfrozen tissue longitudinally and radially arranged about said catheter.

* * * * *